(12) United States Patent
Ando et al.

(10) Patent No.: US 6,827,952 B2
(45) Date of Patent: Dec. 7, 2004

(54) LACTIC ACID BACTERIA, FERMENTED SEASONING LIQUID CONTAINING THE SAME, AND A METHOD FOR PRODUCING BREAD

(75) Inventors: Masayasu Ando, Tokyo (JP); Yoshiaki Shinomiya, Tokyo (JP); Natsuko Nakamura, Tokyo (JP)

(73) Assignee: Oriental Yeast Co., Ltd., Tokyo (JP)

( * ) Notice: Subject to any disclaimer, the term of this patent is extended or adjusted under 35 U.S.C. 154(b) by 0 days.

(21) Appl. No.: 10/107,798

(22) Filed: Mar. 28, 2002

(65) Prior Publication Data

US 2003/0035860 A1 Feb. 20, 2003

(30) Foreign Application Priority Data

Mar. 30, 2001 (JP) .......................................... 2001-098734

(51) Int. Cl.$^7$ .............................. A21D 2/00; A23B 4/22; A01N 63/02; C12N 1/20
(52) U.S. Cl. ........................... 426/61; 426/20; 426/335; 435/252.9
(58) Field of Search .................................. 435/41, 252.9; 426/61, 19, 23, 26, 335, 321, 20, 25

(56) References Cited

U.S. PATENT DOCUMENTS 5,965,414 A * 10/1999 Vandenbergh et al. ...... 435/170

FOREIGN PATENT DOCUMENTS

| JP | 4-4869 | 1/1992 |
| JP | 6-271415 | 9/1994 |
| JP | 7-32702 | 4/1995 |

OTHER PUBLICATIONS

Appl. Microbiol Biotechnol (1998) 50: 253–256; vol. 50 p253–256; A. Corsetti et al.; "Antimould activity of sourdough lactic acid bacteria: identification of a mixture of organic acids produced by *Lactobacillus Sanfrancisco* CB1".

Appl. Environ. Microbiol. (Jan. 2001) vol. 67 p. 1–5; Jesper Magnusson et al.; "*Lactobacillus coryniformis* subsp. *Coryniformis* Strain Si3 Produces a Broad–Spectrum Proteinaceous Antifungal Compound.".

Appl. Environ. Microbiol. (2000) vol. 66 p. 4084–4090; Paola Lavermicocca et al.;"Purification and Characterization of Novel Antifungal Compounds from the Sourdough *Lactobacillus platarum*Strain 21B.".

* cited by examiner

Primary Examiner—Keith Hendricks
(74) Attorney, Agent, or Firm—Armstrong, Kratz, Quintos, Hanson & Brooks, LLP

(57) ABSTRACT

*Lactobacillus sanfranciscencis* strains according to the present invention having a property for producing a non-organic acid antibacterial agent which exhibits at least mold-proofing activity. A fermented seasoning liquid of *Lactobacillus* according to the present invention may contain a *Lactobacillus* strain having a property for producing an antibacterial agent that inhibits the growth of mold. A method for producing bread according to the present invention may involve the use of a fermented seasoning liquid of a *Lactobacillus* strain having a property for producing an antibacterial agent which inhibits the growth of mold to make bread.

17 Claims, No Drawings

LACTIC ACID BACTERIA, FERMENTED SEASONING LIQUID CONTAINING THE SAME, AND A METHOD FOR PRODUCING BREAD

BACKGROUND OF THE INVENTION

1. Field of the Invention

The present invention relates to novel strains of lactic acid bacteria *Lactobacillus sanfranciscencis* having a property of producing an antibacterial agent exhibiting mold-proofing activity, a fermented seasoning liquid containing the bacteria which can be suitably added to food products to inhibit the generation of acidic smell, and a method for producing bread using the fermented seasoning liquid.

2. Description of the Related Art

Antibacterial agents produced by various microorganisms have been studied. Those antibacterial agents should be, when utilized in, for example, the food industry, harmless and less likely to degrade the flavor of the food products. Therefore, very limited number of antibacterial agents and microorganisms producing them are currently used in practice.

Among a variety of microorganisms, lactic acid bacteria have been conventionally contained in or added to various food products including dairy products such as yogurt since the antibacterial agents produced by them have been considered to be advantageous in that they are harmless and less likely to degrade the flavors of the food products. Examples of known antibacterial agents produced by lactic acid bacteria include organic acids such as lactic acid, hydrogen peroxide, and low molecular weight compounds such as diacetyl, as well as proteins including Nisin produced by *Lactococcus lactis* and diplococcin produced by *Lactococcus cremoris*, which have been used as yogurt and cheese starters.

Although those antibacterial agents can inhibit the growth of bacteria, however, they cannot disadvantageously inhibit the growth of, for example, mold or yeast. Mold may be a great menace to almost all kinds of food products since it could be the major cause for the rotting of foods. Therefore, it is important to inhibit the growth of mold in the food industry as much as possible.

Very few lactic acid bacteria have been reported which produce antibacterial agents that can inhibit the growth of mold, including *Lactobacillus plantrum* which produces, as antibacterial agents, organic acids such as phenyl lactic acid (see, for example, Paola Lavermicocca et al. Applied and Environmental Microbiology, September 2000, pp. 4084–4090, vol. 66, No. 9). However, those organic acids such as phenyl lactic acid may not have sufficient mold-proofing activity. Therefore, discovery or development of an antibacterial agent which can effectively inhibit the growth of, for example, mold and be harmless and less likely to degrade the flavor of food products as well as a novel lactic acid bacterium which produce the antibacterial agent are strongly demanded.

SUMMARY OF THE INVENTION

The object of the present invention is to provide: novel strains of lactic acid bacteria *Lactobacillus sanfranciscencis* having a property for producing an antibacterial agent which inhibits growth of mold (or exhibit mold-proofing activity); a fermented seasoning liquid containing any of the *Lactobacillus sanfranciscencis* strains which can be preferably used in food products such as bread dough, inhibit or mask acrid acidic acidic smell and/or sour taste without degrading the flavor of the food products, and exhibit antibacterial activities such as mold-proofing activity; and a method for efficient production of delicious bread that exhibits resistance to bacteria such as mold while inhibiting the generation of or masking acrid acidic acidic smell and/or sour taste.

The *Lactobacillus sanfranciscencis* strains according to the present invention have a property for producing an antibacterial agent which inhibits growth of mold.

A fermented seasoning liquid of *Lactobacillus* according to the present invention comprises *Lactobacillus sanfranciscencis* according to the present invention having a property for producing an antibacterial agent or agents that can inhibit the growth of mold.

A method for producing a bread according to the present invention uses a fermented seasoning liquid of *Lactobacillus lactic* acid bacterium having a property for producing an antibacterial agent which inhibits mold.

DESCRIPTION OF THE PREFERRED EMBODIMENTS

[*Lactobacillus sanfranciscencis*]

The *Lactobacillus sanfranciscencis* strains according to the present invention have been deposited at International Patent Organism Depositary (Tsukuba, Japan) of National Institute of Advanced Industrial Science and Technology (AIST) as FERM P-18244, FERM P-18245 and FERM P-18246.

The *Lactobacillus sanfranciscencis* strains according to the present invention are novel strains of *Lactobacillus sanfranciscencis* that can produce an antibacterial agent or agents described below.

The antibacterial agents produced by the *Lactobacillus sanfranciscencis* strains according to the present invention can inhibit the growth of mold (or exhibit mold-proofing role) as well as growth of yeast. Bacterinocin which can inhibit the growth of bacteria is known as one of antibacterial agents produced by lactic acid bacteria. On the other hand, antibacterial agents produced by the *Lactobacillus sanfranciscencis* strains according to the present invention can inhibit the growth of not only bacteria but also mold and yeast and thus can be useful in the food production industry or the like in which mold-proofing is very important.

Such antibacterial agents can be secreted by the *Lactobacillus sanfranciscencis* strains according to the present invention into a culture solution. Therefore, these antibacterial agents can be easily isolated from the *Lactobacillus sanfranciscencis* cells by, for example, centrifugation and subsequent filtration of a culture solution (fermented solution) of the *Lactobacillus sanfranciscencis* according to the present invention.

Those antibacterial agents are not organic acids while the above-described phenyl lactic acid produced by *Lactobacillus plantrum* which inhibits the growth of mold is an organic acid. In other words, those antibacterial agents produced by the bacteria according to the present invention are distinct from other antibacterial agents such as phenyl lactic acid produced by *Lactobacillus plantrum* and may have a higher antibacterial role when compared to the latter.

Those antibacterial agents produced by the bacteria according to the present invention are thermostable (non-organic acids) and will not lose their antibacterial activities even after a culture solution of the *Lactobacillus sanfranciscencis* according to the present invention is autoclaved. Therefore, these antibacterial agents can be used after a culture solution (fermented solution) of *Lactobacillus san-*

*franciscencis* according to the present invention is sterilized by autoclaving.

The *Lactobacillus sanfranciscensis* strains according to the present invention are gram-positive asporogenic bacilli and belong to the genus *Lactobacillus* which are anaerobiotic or facultative anaerobic. The *Lactobacillus sanfranciscencis* according to the present invention can be isolated from other lactic acid bacteria according to any of known methods.

The *Lactobacillus sanfranciscencis* strains according to the present invention are oleic acid-auxotrophic and, unlike other conventional lactic acid bacteria belonging to the genus *Lactobacillus*, viable in crops (such lactic acid bacteria may sometimes be referred to as "lactic acid bacteria"), which have been isolated from rye sour dough. Accordingly, the *Lactobacillus sanfranciscencis* according to the present invention can be separated from other lactic acid bacteria belonging to the genus *Lactobacillus* by using as an indicator the presence or absence of oleic acid-auxotrophy.

The *Lactobacillus sanfranciscencis* strains according to the present invention can also be separated from other lactic acid bacteria belonging to the genus *Lactobacillus* by using as an indicator the presence or absence of dissolution of calcium carbonate since they are acidogenic bacteria and can dissolve calcium carbonate.

The *Lactobacillus sanfranciscencis* strains according to the present invention can also be separated from other lactic acid bacteria belonging to the genus *Lactobacillus* by using as an indicator the presence or absence of maltose-fermenting activity since they exhibit maltose-fermenting activity (i.e., they can utilize maltose as carbon source).

Alternatively, the *Lactobacillus sanfranciscencis* strains according to the present invention can be separated from other lactic acid bacteria belonging to the genus *Lactobacillus* by using as an indicator the presence or absence of lactose-fermenting activity since, unlike other conventional lactic acid bacteria, they do not exhibit lactose-fermenting activity (i.e., they cannot utilize lactose as carbon source).

The *Lactobacillus sanfranciscencis* strains according to the present invention are heterofermenters and produce 10-fold or more lactic acids with respect to acetic acid (by weight). Generally, in a case of heterofermenter *Lactobacillus brevis*, an equal amount of lactic acid in respect to acetic acid (by weight) is produced, thus produces less amount of acetic acid when compared to that produced by other heterofermenters. Therefore, the *Lactobacillus sanfranciscencis* strains according to the present invention can be separated from other lactic acid bacteria belonging to the genus *Lactobacillus* by using as an indicator the ratio (by weight) of acetic to lactic acid produced by them.

The *Lactobacillus sanfranciscencis* strains according to the present invention may be available from International Patent Organism Depositary (Tsukuba, Japan) of National Institute of Advanced Industrial Science and Technology (AIST), or may be isolated from lactic acid bacteria belonging to the genus *Lactobacillus* using as an indicator any one of the above-described characteristics. In the latter case, isolation may be performed by, for example, screening lactic acid bacteria belonging to the genus *Lactobacillus* using an indicator the presence or absence of oleic acid-auxotrophy, calcium carbonate dissolution, maltose-fermenting activity or others, growing the selected bacteria using a supernatant of an autoclaved solution of yeast autolysate (fresh yeast extract), and examining the presence or absence of the production of the antibacterial agent or agents.

[Fermented Seasoning Liquid of *Lactobacillus*]

A fermented seasoning liquid of *Lactobacillus* according to the present invention may contain the *Lactobacillus sanfranciscencis* according to the present invention and optionally other component or components as required.

The *Lactobacillus sanfranciscencis* according to the present invention may be present in the fermented seasoning liquid of *Lactobacillus* according to the present invention at any suitable amount, and particularly in such an amount that it may produce a sufficient amount of antibacterial agent to exhibit enough antibacterial role in the seasoning liquid. This amount may be selected depending on a particular purpose.

For food products, additional components which can be contained in the fermented seasoning liquid according to the present invention include, but not limited to, for example, any known food additives, seasonings, food colorings and preservatives, and can be suitably selected depending on a particular purpose.

The fermented seasoning liquid of *Lactobacillus* according to the present invention may comprise the *Lactobacillus sanfranciscencis* according to the present invention and therefore antibacterial agents produced by them. The antibacterial agents should be able to inhibit the growth of, at least, mold (i.e., exhibit mold-proofing activity) and preferably yeast as well. When an antibacterial agent can inhibit the growth of both mold and yeast, the activity to inhibit microbial growth may sometimes be referred to as "an antifungal activity" while the antibacterial agent as "an antifungal agent".

A culture solution of the *Lactobacillus sanfranciscencis* according to the present invention can be directly used as the fermented seasoning liquid of *Lactobacillus* according to the present invention without crushing the *Lactobacillus* cells since the above-described antibacterial agent or agents may be secreted by the *Lactobacillus sanfranciscencis* cells. Accordingly, the fermented seasoning liquid of *Lactobacillus* according to the present invention can be prepared very easily.

It should be noted that fermented seasoning liquids of *Lactobacillus* according to the present invention include those comprising the above-described *Lactobacillus sanfranciscencis* as well as those comprising a supernatant obtained by, for example, centrifugation and subsequent filtration of the *Lactobacillus sanfranciscencis* cells.

The fermented seasoning liquid of *Lactobacillus* according to the present invention may comprise at least the *Lactobacillus sanfranciscencis* according to the present invention as the *Lactobacillus* lactic acid bacterium and optionally additional bacterium or bacteria provided the additional bacterium or bacteria may not deteriorate the effect of the present invention, though it may preferably comprise, as *Lactobacillus* lactic acid bacterium, the *Lactobacillus sanfranciscencis* according to the present invention alone.

The fermented seasoning liquid of *Lactobacillus* according to the present invention can be sterilized by, for example, autoclaving since the above-described antibacterial agents are thermostable and thus will not lose their antibacterial role by autoclaving, which may be advantageous in terms of preservation or others. The above-described antibacterial agents are non-organic acids, and any known antibacterial organic acids such as phenyl lactic acid or caproic acid may not be detected in the fermented seasoning liquid of *Lactobacillus* according to the present invention.

Since a fermented seasoning liquid of *Lactobacillus* according to the present invention contains live *Lactobacillus* cells, once it is added to, for example, food products, the bacterium may be fermented in the food products to further produce the above-described antibacterial agent or agents, and organic acids are produced by heterofermentation to reduce the pH of the food products. This can advantageously provide enhanced antibacterial activities such as mold-proofing activity as described above. Moreover, the fermented seasoning liquid that contains the *Lactobacillus sanfranciscencis* strain or strains according to the present invention may be advantageous in that it can be preferably added to, for example, food products without degrading their flavor since acidic smell which is characteristic of acetic acid may not be produced due to small percentage of acetic acid relative to the total organic acids produced by the heterofermentation.

A fermented seasoning liquid of *Lactobacillus* according to the present invention can be suitably used in various fields, and preferably added to, for example, food products.

Food products preferably include, but not limited to, grain-based food products such as bread, confectionery, soft drinks, sugars and liquors, and can be selected depending on a particular purpose. Among all, bread are particularly preferable since addition of the fermented seasoning liquid according to the present invention can provide, when added to bread, a soft eating quality, a longer shelf-life in storage and masking of powder smell (caused by wheat flour) and/or oxidized odor (caused by oils and fats) without giving acidic smell.

The fermented seasoning liquid of *Lactobacillus* according to the present invention may be added to food products at any amount provided that it contains sufficient live bacterial cells to provide the effect of the present invention. This amount may be suitably selected depending on a particular purpose, the type of the food product, and the like. For example, the fermented seasoning liquid of *Lactobacillus* according to the present invention may typically be added to bread at an amount of $1.0 \times 10^8$ CFU/g or more in order to provide sufficient antibacterial effect.

For bread, the fermented seasoning liquid of *Lactobacillus* according to the present invention may be added preferably to ingredients of bread, and more particularly to dough during mixing step so as to obtain maximum antibacterial effect.

Bread may be produced by, for example, but not limited to, sponge dough method, straight dough method and liquid dough method, and preferably by sponge dough method in which the *Lactobacillus sanfranciscencis* according to the present invention can be fermented in bread dough.

The present invention will be described in reference to the following examples though it may not be limited to these examples.

EXAMPLE 1 AND COMPARATIVE EXAMPLE 1

*Lactobacillus sanfranciscencis* strains according to the present invention (FERM P-18244, 18245 and 18246) have been isolated from lactic acid bacteria as described below. Particularly, a lactic acid bacterium sample was diluted, inoculated on GYP and MYP white agar media and cultured at 30–35° C. for 3–7 days. Colonies of acidogenic bacteria that formed halo were then selected, probed, and inoculated and cultured on a stock medium.

Next, for easy identification of bacteria, the morphological examination, oleic acid-auxotrophy test, and lactose- and maltose-fermentation tests were performed on the bacteria. Oleic acid-auxotrophic bacilli which exhibited not lactose- but maltose-fermenting activity were selected and isolated. These lactic acid bacteria isolated were then inoculated (at $1.0 \times 10^6$ CFU/ml) on a liquid growth medium for lactic acid bacteria culture at 30° C. (the composition of the culture medium will be described below) followed by stationary culture at 30° C. for 48 hours.

[Liquid Medium for Lactic Acid Bacteria Culture (Modified Sourdough Medium)]

Maltose . . . 2.0%

Yeast Extract . . . 1.0%

Tween 80 . . . 0.03%

Trypticase/peptone (BBL) . . . 0.5% pH=6.5 (NaOH), 121° C., 15 minutes, sterilized by autoclaving

Next, test group (Example) and control group (comparative experiments) were examined as will be described below. Particularly, for the control group (comparative experiments) only a mixture medium comprising the culture supernatant obtained above and a fresh YPD medium (yeast extract 1.0%, polypeptone 2.0% and glucose 2.0%) (1:1) were used. For the test group (Example), yeast *Saccharomyces cerevisiae* was inoculated on the above-described mixture medium, subjected to stationary culture at 25–30° C. for 48 or 72 hours and then cultured for 3 days. Absorbance was determined at OD660 nm to evaluate the growth of the yeast cells in the culture solution.

The results for the control group (control experiments) were as follows: 0.04 at OD 660 nm immediately after mixing with the mixture medium; 9.4 at OD660 nm after 48 hours; and 9.6 at OD660 nm after 72 hours.

On the other hand, the results for the test group (Example) were: 0.05 at OD 660 nm immediately after inoculation of the yeast cells on the mixture medium; 1.5 at OD660 nm after 48 hours; and 5.8 at OD660 nm after 72 hours. The lactic acid bacterium strain used in the test group (Example) was *Lactobacillus sanfranciscencis* FERM P-18246. The results are shown in Table 1 below.

Next, the procedure described above was repeated for each of other lactic acid bacterium strains listed in Table 1 instead of FERM P-18246. The results are also shown in Table 1.

| | Absorbance (OD660 nm) | | | | | |
|---|---|---|---|---|---|---|
| | Immediately after inoculation | | After 48 hours | | After 72 hours | |
| Strain used for preparation of supernatant | control group | Test group | control group | Test group | control group | Test group |
| *Lb. sanfranciscensis* SDB-5 *1 | 0.04 | 0.05 | 9.4 | 1.5 | 9.6 | 5.8 |
| *Lb. sanfranciscensis* SDB-2 | 0.05 | 0.05 | 9.5 | 3.8 | 9.8 | 8.2 |
| *Lb. sanfranciscensis* ATCC27651 | 0.05 | 0.04 | 9.6 | 8.5 | 9.7 | 10.6 |

-continued

| | Absorbance (OD660 nm) | | | | | |
|---|---|---|---|---|---|---|
| | Immediately after inoculation | | After 48 hours | | After 72 hours | |
| Strain used for preparation of supernatant | control group | Test group | control group | Test group | control group | Test group |
| Lb. brevis ATCC4006 | 0.04 | 0.04 | 9.3 | 6.9 | 9.4 | 10.1 |
| Lb. plantrum IF03074 | 0.05 | 0.05 | 9.5 | 9.1 | 9.5 | 11.2 |

*1 is a FERM P-18246 strain

It is apparent from the results shown in Table 1 above that the culture solution (fermented solution) of *Lactobacillus sanfranciscencis* FERM P-18246 according to the present invention has an ability to inhibit the growth of yeast.

The same procedure was repeated except for using *Candida albicans, Pichia farinose* or *Debaryomyces hansenii* instead of yeast *Saccharomyces cerevisiae*. The same results were obtained as those obtained for *Saccharomyces cerevisiae*.

EXAMPLE 2 AND COMPARTIVE EXAMPLE 2

*Lactobacillus sanfranciscencis* FERM P-18246 according to the present invention was isolated according to the procedure described in Example 1 and inoculated (at $1.0 \times 10^6$ CFU/ml) on the above-described liquid growth medium for lactic acid bacterium culture followed by stationary culture at 30° C. for 48 hours to prepare a solution containing the bacterium ($1.0 \times 10^{10}$ CFU/g).

Next, a dough for overnight sponge dough method was prepared as described below. Mixing was performed at flow-speed for 2 minutes and at medium speed for 1.5 minutes (L2M1.5). The dough was pre-kneaded at 22° C. and then fermented at 22° C., 85RH % for 14–16 hours.
[Dough for Overnight Sponge Dough Method]

wheat flour (strong flour) . . . 70% by weight
yeast . . . 2.2% by weight
dough improver . . . 0.1% by weight
Bacterium solution . . . 1% by weight
Water . . . 40% by weight The dough for overnight sponge dough method was kneaded using the conditions described below and then divided into 6 pieces: 200 g each (pullman); bench time: 20 minutes; shaping the dough into a one-loaf form which was then folded in two and packed in a mold, final proven fermentation (at 35° C., 80RH %, for 50–55 minutes) and baking (at 210° C. for 35 minutes) to make a loaf of bread. During kneading step, mixing was performed at low speed for 1 minute and at medium speed for 3 minutes (L1M3) at 27° C. (floor time: 20 minutes).
<Kneading> wheat flour (strong flour) . . . 30% by weight
salt . . . 2% by weight
sugar . . . 6% by weight
skimmed milk powder . . . 2% by weight
shortening . . . 5% by weight
water . . . 25% by weight Thus obtained loaf of bread was tested for resistance against mold (Strains: *Aspergillus niger, Penicillum chrysogenum, Aspergillus oryzae* var. *brunneus, Rhizopus oryzae, Penicillum citrium, Penicillum funiculosum, Mucor hiemalis f. hiemalis*) by inoculating each of the test strains to a slice of the baked bread (at 9 spots for each strain, about 10 cells/spot)). Mold colonies appeared 4 days after inoculation in Comparative Example 2 in which the above-described bacterium solution was not used while colonies appeared 6 days after inoculation in Example 2 in which the above-described bacterium solution was used. In summary, the appearance of mold colonies was delayed by about 2 days in the latter. The results are shown in Table 2.

Next, a dough for 4-hour sponge dough method was prepared using the compositions listed below. Mixing was performed at flow-speed for 2 minutes and at medium speed for 1.5 minutes (L2M1.5). The dough was pre-kneaded at 24° C. and then fermented at 24° C., 80RH % for 4 hours.
<Dough for 4-Hour Sponge Dough Method> wheat flour (strong flour) . . . 70% by weight
yeast . . . 2.2% by weight
dough improver . . . 0.1% by weight
bacterium solution . . . 1% by weight
water . . . 40% by weight The dough for 4-hour sponge dough method was kneaded using the conditions described below and then final-conditioned for baking (divided into 6 pieces: 220 g each (pullman); venting time: 20 minutes; shaping the dough into a one-loaf form which was then folded in two and packed in a mold), final proven fermentation (at 35° C., 80RH %, for 50–55 minutes) and baking (at 210° C. for 35 minutes) to make a loaf of bread. During kneading step, mixing was performed at low speed for 1 minute, at medium speed for 3 minutes, and after adding shortening, at medium speed for 3 minutes and at high speed for 1 minute (L1M3IM3H1) at 27° C. (floor time: 20 minutes).
<Kneading> wheat flour (strong flour) . . . 30% by weight
salt . . . 2% by weight
sugar . . . 6% by weight
skimmed milk powder . . . 2% by weight
shortening . . . 5% by weight
water . . . 27% by weight Thus obtained loaf of bread was tested for resistance against mold (Strains: *Aspergillus niger, Penicillum chrysogenum, Aspergillus oryzae* var. *brunneus, Rhizopus oryzae, Penicillum citrium, Penicillum funiculosum, Mucor hiemalis f. hiemalis*) by inoculating each of the test strains on a slice of the baked bread (at 9 spots for each strain, about 10 cells/spot). Mold colonies appeared 4 days after inoculation in Comparative Example 2 in which the above-described bacterium solution was not used while colonies appeared 5 days after inoculation in Example 2 in which the above-described bacterium solution was used. In summary, the appearance of mold colonies was delayed by about 1 day in the latter. The results are shown in Table 2.

| Storage (28° C.) | Sponge dough method (loaf of bread) | | Overnight sponge dough method (loaf of bread) | |
|---|---|---|---|---|
| | no additive | liquid medium of lactic acid addedd | no additive | liquid medium of lactic acid addedd |
| Day 1 | − | − | − | − |
| Day 2 | − | − | − | − |
| Day 3 | − | − | − | − |
| Day 4 | + | − | ± | − |
| Day 5 | ++ | ± | + | − |
| Day 6 | +++ | + | ++ | ± |

In Table 2 above, "−" means that no mold colony was detected, "±" means that few colonies were detected, "+" means that small colonies were detected, "++" means that many colonies were dotted, and "+++" means that colonies were abundant.

The present invention can provide: novel strains of *Lactobacillus sanfranciscencis* which produce an antibacterial agent or agents that may inhibit the growth of mold (or exhibit mold-proofing activity); a fermented seasoning liquid of the *Lactobacillus sanfranciscencis* strains which can be preferably used in food products such as bread dough, inhibit or mask acrid acidic smell and/or sour taste without degrading the flavor of the food products, and exhibit antibacterial activities such as mold-proofing activity; and a method for efficient production of delicious bread that exhibits resistance to bacteria such as mold while inhibiting the generation of or masking acrid acidic smell and/or sour taste.

What is claimed is:

1. An isolated *Lactobacillus sanfranciscencis* compromising, at least one *Lactobacillus sanfranciscencis* strain selected from FERM P-18244, FERM P-18245 and FERM P-18246, wherein the *Lactobacillus sanfranciscencis* strain has a property for producing an antibacterial agent which inhibits growth of mold and growth of yeast.

2. An isolated *Lactobacillus sanfranciscencis* according to claim 1, wherein the antibacterial agent is a thermostable non-organic acid.

3. An isolated *Lactobacillus sanfranciscencis* according to claim 1, wherein the isolated *Lactobacillus sanfranciscencis* is an oleic acid-auxotrophic, acid-producing bacterium and exhibits maltose-fermenting activity.

4. The isolated *Lactobacillus sanfranciscencis* according to claim 1, wherein the isolated *Lactobacillus sanfranciscencis* is a heterofermenter and produces 10-fold or more lactic acid with respect to acetic acid by weight.

5. A fermented seasoning liquid of *Lactobacillus* comprising at least one *Lactobacillus sanfranciscencis* strain selected from FERM P-18244, FERM P-18245 and FERM P-18246. wherein the *Lactobacillus sanfranciscencis* strain has a property for producing an antibacterial agent which inhibits growth of mold.

6. The fermented seasoning liquid of *Lactobacillus* according to claim 5, wherein the antibacterial agent inhibits growth of yeast.

7. A fermented seasoning liquid of *Lactobacillus* according to claim 5, wherein the antibacterial agent is a thermostable non-organic acid.

8. A fermented seasoning liquid of *Lactobacillus* according to claim 5, wherein the *Lactobacillus sanfranciscencis* strain is oleic acid auxotrophic, acid-producing bacterium and exhibits maltose-fermenting activity.

9. A fermented seasoning liquid of *Lactobacillus* according to claim 5, wherein the fermented seasoning liquid of *Lactobacillus* contains live cells of the *Lactobacillus sanfranciscencis* strain.

10. A fermented seasoning liquid of *Lactobacillus* according to claim 9, wherein the fermented seasoning liquid of *Lactobacillus* is added to a food product.

11. A fermented seasoning liquid of *Lactobacillus* according to claim 10, wherein the amount of the live cells of the *Lactobacillus sanfranciscencis* strain to be added to the food product is $1.0 \times 10^8$ CFU/g or more.

12. A fermented seasoning liquid of *Lactobacillus* according to claim 10, wherein the food product is an ingredient to be used for bread making.

13. A method for producing a bread comprising the step of:
    fermenting a bread dough to which a fermented seasoning liquid of *Lactobacillus* is added,
    wherein the fermented seasoning liquid of *Lactobacillus* comprises at least one *Lactobacillus sanfranciscencis* strain selected from FERM P-18244, FERM P-18245 and FERM P-18246, wherein the *Lactobacillus sanfranciscencis* strain produces an antibacterial agent which inhibits mold, and said fermented seasoning liquid comprises live cells of the *Lactobacillus sanfranciscencis* strain.

14. A method for producing a bread according to claim 13, wherein the antibacterial agent inhibits the growth of yeast.

15. A method for producing a bread according to claim 13, wherein the antibacterial agent is a thermostable, non-organic acid.

16. A method for producing bread according to claim 13, wherein the *Lactobacillus sanfranciscencis* strain is an oleic acid-auxotrophic, acid-producing bacterium and exhibits maltose-fermenting activity.

17. A method for producing a bread according to claim 13, wherein the amount of the live cells of the *Lactobacillus sanfranciscencis* strain to be added to a food product is $1.0 \times 10^8$ CFU/g or more.

* * * * *